(12) United States Patent
Dublin et al.

(10) Patent No.: US 7,672,731 B2
(45) Date of Patent: Mar. 2, 2010

(54) IMPLANTABLE DEVICE INCLUDING MULTIPLE COMMUNICATION ANTENNAS

(75) Inventors: Garry L. Dublin, Maple Grove, MN (US); Gregory J. Haubrich, Champlin, MN (US); Chris C. Fuller, Minneapolis, MN (US); Piotr Przybyszewski, Coon Rapids, MN (US); Len D. Twetan, Excelsior, MN (US); William D. Verhoef, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 786 days.

(21) Appl. No.: 11/109,995

(22) Filed: Apr. 20, 2005

(65) Prior Publication Data
US 2006/0241724 A1 Oct. 26, 2006

(51) Int. Cl.
*A61N 1/02* (2006.01)
(52) U.S. Cl. .......................................... 607/60; 607/36
(58) Field of Classification Search .................... 607/60
See application file for complete search history.

(56) References Cited

U.S. PATENT DOCUMENTS

| | | | | |
|---|---|---|---|---|
| 3,683,389 A * | 8/1972 | David L. Hollis | ........... | 343/788 |
| 4,441,498 A * | 4/1984 | Nordling | ..................... | 607/32 |
| 6,141,588 A | 10/2000 | Cox et al. | | |
| 6,167,312 A | 12/2000 | Goedeke | ....................... | 607/60 |
| 6,169,925 B1 | 1/2001 | Villaseca et al. | ............... | 607/60 |
| 6,240,317 B1 | 5/2001 | Villaseca et al. | ............... | 607/60 |
| 6,405,088 B1 | 6/2002 | Merlin et al. | .................. | 607/60 |
| 6,434,429 B1 | 8/2002 | Kraus et al. | .................... | 607/60 |
| 6,456,256 B1 | 9/2002 | Amundson et al. | .......... | 343/873 |
| 6,463,329 B1 | 10/2002 | Goedeke | | |
| 6,675,045 B2 | 1/2004 | Mass et al. | ..................... | 607/32 |
| 6,708,065 B2 | 3/2004 | Von Arx et al. | ................ | 607/60 |
| 7,317,946 B2 * | 1/2008 | Twetan et al. | .................. | 607/60 |
| 2003/0025645 A1 | 2/2003 | Amundson et al. | .......... | 343/873 |
| 2003/0189518 A1 | 10/2003 | Johnson et al. | | |
| 2004/0106967 A1 | 6/2004 | Von Arx et al. | | |
| 2004/0215280 A1 | 10/2004 | Dublin et al. | | |

OTHER PUBLICATIONS

International Search Report for counterpart International Application No. PCT/US2006/013614, dated Aug. 14, 2006.

* cited by examiner

*Primary Examiner*—Kennedy J Schaetzle

(57) ABSTRACT

An implantable device, such as an implantable medical device (IMD) includes at least two radio frequency (RF) antennas and may additionally include an RF communication circuit. The RF antennas are spatially diverse, are disposed adjacent a housing, and are each configured to receive RF signals transmitted to the IMD from a remote RF signal source. The RF communication circuit, if included, is disposed within the housing and is configured to selectively receive the RF signals received by one or more of the spatially diverse RF antennas.

24 Claims, 4 Drawing Sheets

IMPLANTABLE DEVICE INCLUDING MULTIPLE COMMUNICATION ANTENNAS

FIELD OF THE INVENTION

The present invention relates to implantable devices and, more particularly, to an implantable device that includes a plurality of communication antennas.

BACKGROUND OF THE INVENTION

Various types of devices have been developed for implantation into the human body to provide various types of health-related therapies and/or monitoring. Examples of such devices, generally known as implantable medical devices (IMDs), include cardiac pacemakers, cardioverter/defibrillators, cardiomyostimulators, various physiological stimulators including nerve, muscle, and deep brain stimulators, various types of physiological monitors, and drug delivery systems, just to name a few. Some IMDs include varying amounts of electronic memory that may be used to store not only device operating and control software, but to store various types of patient- and device-related data. In addition, some of these same IMDs may include signal processing and telemetry circuitry, which allows some or all of the data stored in the memory to be transmitted to a remote computer network or other communication node, and/or the device to receive and store data transmitted to it remotely from a computer network or other communication node, via a communication link.

More recently, the above-mentioned communication link is implemented using radio frequency (RF) communication techniques. As compared to previous techniques, using RF communication generally increases the range over which communication between the IMD and a communication node can occur. Although RF communication is generally safe and reliable, it can exhibit certain drawbacks. For example, RF communication can exhibit multipath fading or distortion, which can result from multiple reflections of the transmitted signal between an RF transmitter and an RF receiver. Such multipath fading and/or distortion can adversely impact the ability to implement RF communication between an IMD and an external communication node.

Hence, there is a need for a system that can compensate for multipath fading and/or distortion that can occur when RF communication is occurring between an IMD and an external communication node. The present invention addresses one or more of these needs. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

In one exemplary embodiment, an implantable device includes a housing, and at least two radio frequency (RF) antennas. The RF antennas are disposed adjacent the housing, and are each configured to receive RF signals transmitted to the device from a remote RF signal source and to emit RF signals to one or more other device.

In another exemplary embodiment, an implantable medical device (IMD) includes a housing, at least two radio frequency (RF) antennas, and an RF communication circuit. The RF antennas are spatially diverse, and each is configured to receive RF signals transmitted to the IMD from a remote RF signal source and to emit RF signals to one or more remote devices. The RF communication circuit is disposed within the housing and is configured to selectively receive the RF signals received by one or more of the spatially diverse RF antennas and supply the RF signals emitted by one or more of the spatially diverse antennas.

BRIEF DESCRIPTION OF THE DRAWINGS

The present invention will hereinafter be described in conjunction with the following drawing figures, wherein like numerals denote like elements, and wherein.

DETAILED DESCRIPTION OF THE INVENTION

The following detailed description of the invention is merely exemplary and is not intended to limit the invention or the application and uses of the invention. Furthermore, there is no intention to be bound by any theory presented in the preceding background of the invention or the following detailed description of the drawings. In this regard, before proceeding with the detailed description, it is to be appreciated that the described embodiment is not limited to use in conjunction with a specific type of implantable device. Thus, although the present embodiment is, for convenience of explanation, depicted and described as being implemented in an implantable medical device (IMD), and more specifically an implantable cardioverter-defibrillator (ICD), it will be appreciated that it can be implemented in any one of numerous other types of IMDs, or any one of numerous other types of implantable devices, which may or may not be configured to deliver medical therapy. In addition, although the present embodiment is depicted and described as being implemented with two antennas, it will be appreciated that the implantable devices encompassed herein could be implemented, if needed or desired, with more than two antennas.

Figure 1:
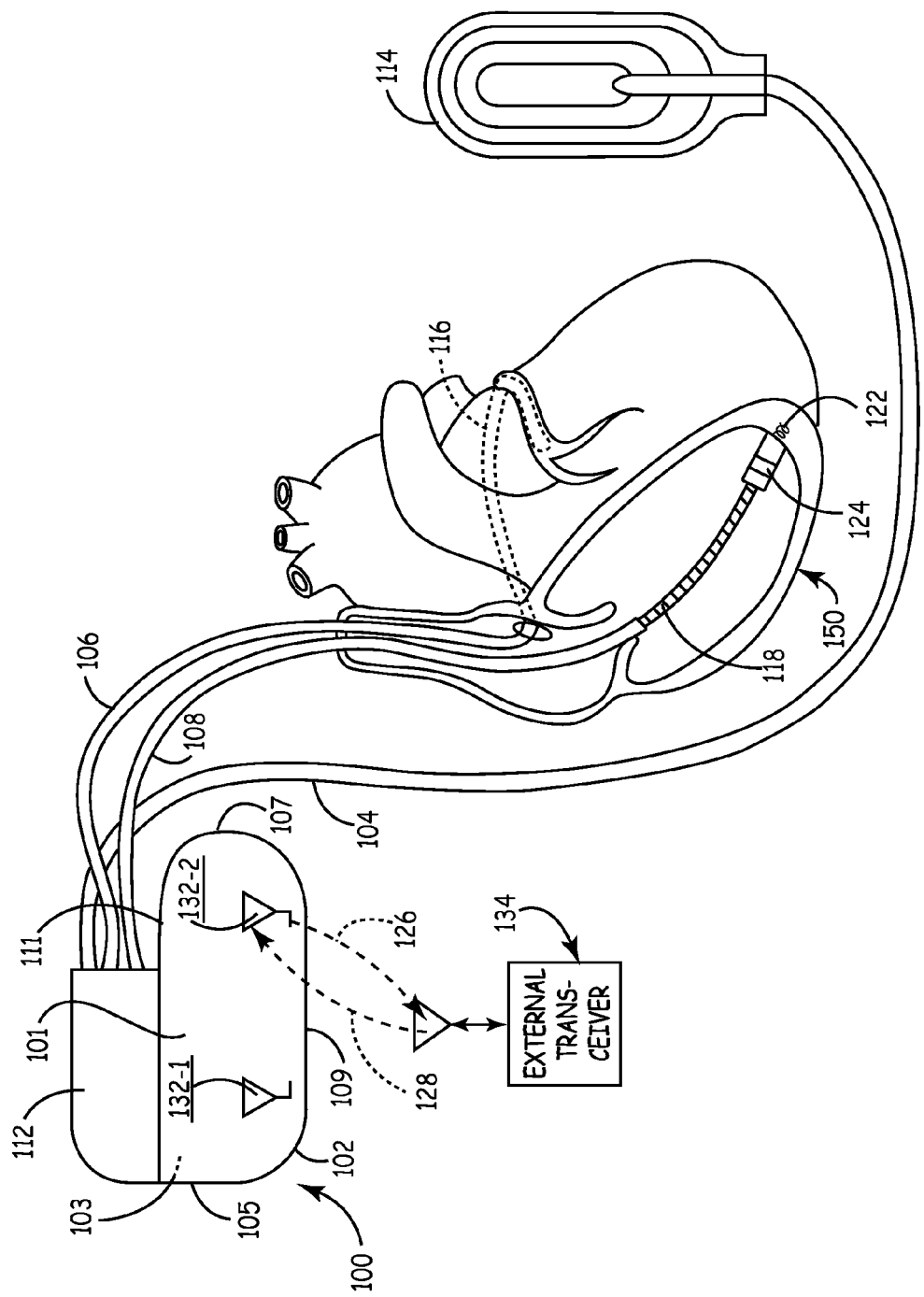
FIG. 1 is a perspective view of an implantable cardio-defibrillator coupled to a heart and which is exemplary of one type of implantable medical device (IMD) that may incorporate an embodiment of the present invention.

Turning now to the description and with reference first to FIG. 1, a simplified representation of an IMD 100 that is implemented as an ICD and its connection to a patient heart 150 is shown. The IMD 100 includes a housing 102 and a plurality of therapy leads, including a first therapy lead 104, a second therapy lead 106, and a third therapy lead 108. The housing 102 is preferably formed of a suitable, internal body compatible material that has been approved for medical use, such as, for example, titanium. In one embodiment, which is discussed further below, at least portions of the housing 102 are also formed of a suitable conductive material. The housing 102 is preferably hermetically sealed, so that it is substantially impervious to body fluids, and is suitably physiologically shaped to substantially avoid any sharp edges, so that tissue damage during and after implantation can be substantially avoided. In the depicted embodiment, the housing 102 includes at least a first side surface 101, a second side surface 103 (not visible in FIG. 1), a first end surface 105, a second end surface 107, a bottom surface 109, and a top surface 111.

The housing 102 additionally includes a connector header 112 that is disposed on, or is formed as part of, the housing top surface 111. The connector header 112 includes separate connector ports and feedthroughs (neither are shown), at least one for each therapy lead 104-108. The connector ports each electrically couple one of the therapy leads 104-108 to one of the feedthroughs, which in turn electrically couples the connector port to the associated circuitry disposed within the housing 102. A detailed description of at least a portion of this circuitry is provided further below.

The first, second, and third therapy leads 104-108, each of which include a plurality of conductors, extend from the housing 102 and include first, second, and third electrodes, 114, 116, and 118, respectively, that can be used for pacing, sensing, and/or cardioversion/defibrillation. When implanted in a patient, the first therapy lead 104 extends subcutaneously from the housing 102, and the first electrode 114 is mounted in the patient's chest cavity proximate the heart 150. The second therapy lead 106 extends subcutaneously from the housing 102 and into the patient heart 150. Specifically, the second therapy lead 106 extends transvenously into the heart 150 and, more particularly, into the coronary sinus and down any cardiac vein accessible from the coronary sinus. The second electrode 116 is disposed in the heart 150 such that it extends from a point within the opening of the coronary sinus to the vicinity of the left ventricle. Similarly, the third therapy lead 108 extends transvenously into the heart 150 and, more particularly, into the right ventricular chamber, in which the third electrode 118 is disposed. As is generally known, cardioversion-defibrillation shocks may be applied, when needed, between selected pairs of the first 114, second 116, and third 118 electrodes, according to any one of various defibrillation regimens. It is additionally noted that, in the depicted embodiment, the third therapy lead 108 is also terminated with a pair of ventricular pace/sense electrode 122 and 124. These ventricular pace/sense electrodes are used to provide cardiac pacing pulses, and may be additionally employed to provide near field and/or far field EGM ventricular sensing capabilities.

As FIG. 1 additionally shows, the IMD 100 is capable of both transmitting 126 and receiving 128 data. This may be accomplished in any one of numerous ways, but in the depicted embodiment this is accomplished via radio frequency (RF) signal transmission using any one of numerous known RF modulation schemes. Thus, in the depicted embodiment the IMD 100 includes two antennas 132 (132-1, 132-2) that are used, in conjunction with other circuitry disposed within the ICD housing 102, to transmit 126 RF signals to, and to receive 128 RF signals from, one or more external transceivers 134. It will be appreciated that the antennas 132 could be implemented as any one of numerous types of antennas that are capable of receiving and emitting RF signals. For example, the antennas could be implemented as any one of numerous types of monopole antennas, dipole antennas, loop antennas, helical antennas, slot antennas, or patch antennas, just to name a few non-limiting examples. It will additionally be appreciated that the antennas 132 are preferably implemented as the same antenna-type. For example, both antennas are preferably implemented as monopole, dipole, loop, slot, patch, helical, etc. antennas. However, it will be appreciated that each individual antenna 132-1, 132-2 could be implemented as a different type of antenna.

No matter the specific type of antenna (or antennas) used, the internal circuitry, which will be described in more detail further below, is configured, in one embodiment, to select one of the antennas 132-1 (132-2) as the active antenna, which is used to receive and emit RF signals, while the other antenna 132-2 (132-1) is inactive. In another embodiment, all of the antennas 132-1, 132-2 are simultaneously active for RF signal transmission and reception. In this latter embodiment, the internal circuitry and/or software may be configured to align the phases of the RF signals received by all of the antennas 132-1, 132-2, in order to combine the received signals together. Moreover, before proceeding further, it will be appreciated that although the antennas 132 are, for ease of illustration, depicted schematically in FIG. 1, various physical configurations and implementations of the antennas 132 will be depicted and described in more detail further below.

Returning now to the description, the data that the IMD 100 transmits to, and receives from, the external transceiver 134 will depend, at least in part, on the type and purpose of the transceiver 134. For example, the transceiver 134 may be a programming device that a physician or other practitioner uses to program or reprogram the overall operation, or portions thereof, of the IMD 100. Alternatively, the transceiver 134 may be a monitoring device that is used to interrogate the IMD 100 and, in response to the interrogation, receive various data from the IMD 100 for subsequent transmission.

Figure 2:
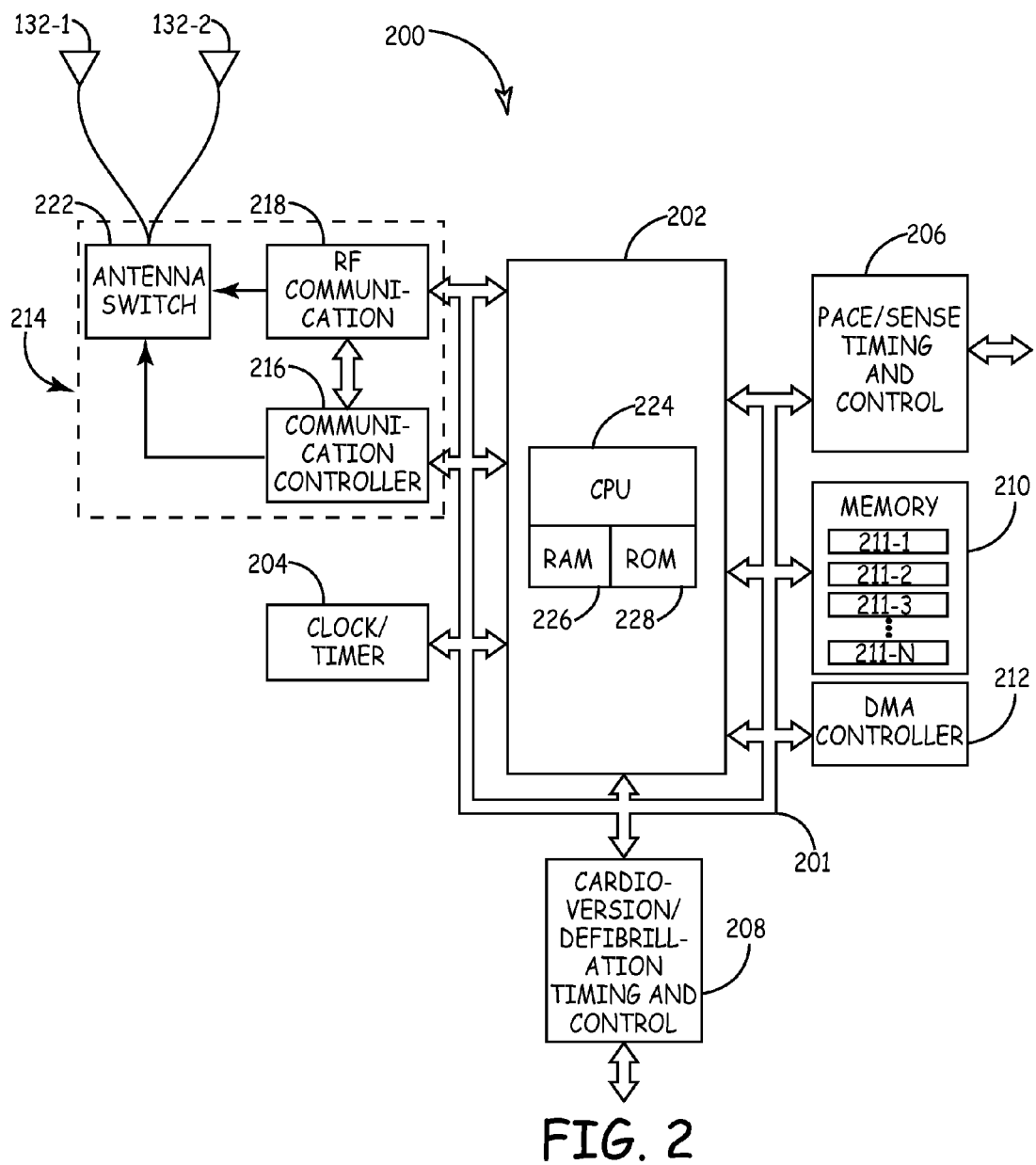
FIG. 2 is a functional block diagram of an exemplary circuit architecture that may be included in the IMD of FIG. 1.

As was noted above, the IMD 100 includes circuitry within the housing 102 that is used to control the overall operation of the IMD 100. At least a portion of this circuitry is illustrated in FIG. 2, and will now be described in detail. Before doing so, however, it will be appreciated that the circuitry depicted in FIG. 2 and described herein is merely exemplary of a particular architecture, and that any one of numerous other circuit architectures may be used to implement the operation of the IMD 100.

Turning now to FIG. 2, circuitry 200 illustrated therein includes a controller circuit 202 and various other functional circuit blocks 204-222 that are in operable communication with, and which may be operated under control of, the controller circuit 202 via, for example, a common communications data bus 201. The controller circuit 202 includes, among other things, a CPU (central processing unit) 224, which may include on-board RAM (random access memory) 226, and on-board ROM (read only memory) 228. The CPU 224 may be any one of numerous known general purpose processors or an application specific processor that operates in response to program instructions. Such program instructions may be stored in either or both the RAM 226 and the ROM 228. For example, the operating system software may be stored in the ROM 228, whereas various operating mode software routines and various operational parameters may be store in the RAM 226. It will be appreciated that this is merely exemplary of one scheme for storing operating software and software routines, and that various other storage schemes may be implemented. It will also be appreciated that the controller circuit 202 may be implemented using various other circuits, not just a programmable processor. For example, digital logic circuits and analog signal processing circuits could also be used.

A clock/timer circuit 204 provides one or more clock and timing signals to the controller circuit 202 and, if needed, to various ones of the other functional blocks 206-224. The clock and timing signals provide for the proper synchronous operation of the various functional circuits that make up the circuitry 200. The clock/timer circuit 204 may be any one of numerous known circuits for providing clock and/or timing signals.

A pace/sense timing and control circuit 206 and a cardioversion/defibrillation timing and control circuit 208 are each coupled to the controller circuit 202 via the communications data bus 201. The pace/sense timing and control circuit 206 is programmable and, in response to instructions from the controller circuit 202, implements various atrial and ventricular pacing operational modes. The pace/sense timing and control circuit 206 may also implement various tachyarrhythmia detection and classification operations. The cardioversion/defibrillation timing and control circuit 208, in response to instructions from the controller circuit 202, delivers cardioversion/defibrillation shock therapy or, if appropriate, pacing pulse therapy, to selected pairs of the first 114, second 116, and third 118 electrodes when an atrial or ventricular fibrillation or flutter, or a malignant high rate tachycardia, is detected.

A memory circuit 210 is in operable communication with the controller circuit 202 via the communications data bus 201. The memory circuit 210 includes a plurality of memory registers 211-1, 211-2, 211-3, . . . 211-N, in which various types of data are stored. The data that the memory circuit 210 stores in its memory registers 211 may include both device-related data and physiological-related data. It will be appreciated that one or more memory circuits 210 may be in operable communication with the controller circuit 202 to store such data. It will also be appreciated that the memory circuit 210 could be integrally formed as part of the controller circuit 202 and/or CPU 220, RAM 222, and/or ROM 224, or could be part of a device or system that is physically separate from the IMD 100. The data that may be stored in memory circuit 210 include, but are not limited to, various types of patient-related data, and various types of device-related data. Some or all of the data stored in the memory circuit 210 may be read and, as was discussed above, transmitted to the external transceiver 134 (see FIG. 1).

In the depicted embodiment, a DMA (direct memory access) controller 212 is in operable communication with the controller circuit 202. The DMA controller 212, as is generally known, provides direct memory access to memory circuit memory registers 211, or to the RAM 226 or ROM 228, without involving the CPU 224. This can conserve battery power and simplify data read and write operations. It will be appreciated that the DMA controller 212 could be omitted or could form an integral part of the controller circuit 202.

As was discussed above, the antennas 132 receive the RF modulated data that is transmitted from, and emit the RF modulated data that is transmitted to, the external transceiver 134. The data that are received from, and emitted by, the antennas 132 are supplied to, and received from, respectively, communication and control circuitry 214. In the depicted embodiment, the communication and control circuit 214 includes a communication controller 216, an RF communication circuit 218, and an antenna switch 222. The communication control circuit 216 is in operable communication with the controller circuit 202, the RF communication circuit 218, and the antenna switch 222 and, in response to instructions received from the controller circuit 202, controls the configuration of the RF communication circuit 218 and the antenna switch 222. More specifically, the communication controller 216 supplies a transmit/receive command signal to the RF communication circuit 214 and a switch control signal to the antenna switch 222. As will be described below, these signals respectively control which antenna or antennas 132 are coupled to the RF communication circuit 218, and configure the RF communication circuit 218 to transmit, receive, or simultaneously transmit and receive RF signals.

The communication controller 216 is configured to receive a signal that is at least representative of the signal strength of the RF signal received by the currently active antenna 132. In the depicted embodiment, the amplitude of the received RF signal is used to determine the received RF signal strength by implementing, for example, an RSSI (received signal strength indicator). It will be appreciated, however, that is merely exemplary, and that the received RF signal strength may be determined using any one of numerous ways of determining received RF signal strength or RF communication link quality. For example, the communication controller 216 could instead be configured to verify the integrity of the data received from the external transceiver 134. No matter how the received RF signal strength is determined, the signal that is representative thereof is preferably supplied to the communication controller 216 from the RF communication circuit 214. In response to this signal, the communication controller 216 supplies the switch control signal to the antenna switch 222, which is used to select one or both of the antennas 132 to function as the active antenna.

In the depicted embodiment, the RF communication circuit 218 is implemented as a transceiver that, in response to the transmit/receive command signal supplied from the communication control circuit 216, is configured as a transmitter, a receiver, or simultaneously as both a transmitter and a receiver. Thus, the RF communication circuit 218, in some embodiments, may additionally include one or more RF signal sources (not shown) that may be used to demodulate data from the RF signals received by the IMD 100, and to modulate data being transmitted by the IMD 100. When the RF communication circuit 218 is configured as a transmitter, the controller circuit 202 supplies data to the RF communication circuit 218, which in turn modulates the data for transmission, via one or more of the antennas 132. Correspondingly, when the RF communication circuit 218 is configured as a receiver, it may appropriately demodulate data from the RF signals received by one or more of the antennas 132, and supply the data to the controller circuit 202. As noted above, in some embodiments the RF communication circuit 218 may be configured to transmit and receive simultaneously.

Although not depicted in FIG. 2, it will be appreciated that in some embodiments an additional processing circuit could be coupled between the controller circuit 202 and the RF communication circuit 218. This additional processing circuit, if included, is configured to convert the data that are transmitted between the RF communication circuit 218 and the controller circuit 202 from a parallel format to serial format, and vice-versa. In other embodiments, if conversion between parallel and serial formats is needed or desired, this functionality could be implemented within the RF communication circuit 218 or the controller 202. Moreover, if the IMD 100 is configured, as was previously mentioned, to use both antennas 132-1, 132-2 to receive RF signals, the RF communication circuit 218 may additionally be configured to align the phases of the RF signals received by both antennas 132-1, 132-2, and then combine the received signals together. Alternatively, a separate circuit could be used to implement this function.

The antenna switch 222, as was noted above, determines which of the antennas 132 is (or are) used to emit RF signals to, and receive RF signals from, the external transceiver 134. As FIG. 2 shows, the antenna switch 222 is in operable communication with both the communication controller 216 and the RF communication circuit 218. The antenna switch 222 is configured to receive the switch control signal supplied from the communication controller 216 and, in response to this signal, selects one of the antennas 132 as the active antennas. Alternatively, as was previously noted, the antenna switch 222 could be configured to select both antennas 132 as the simultaneously active antennas, to improve the overall signal-to-noise ratio, or the IMD 100 could be implemented without the antenna switch 222.

The antennas 132, as was previously noted, are implemented in various physical configurations and are preferably located external to, or are formed integral with, the ICD housing 102 to provide sufficient spatial diversity so that the RF communication circuit 218 has a greater probability of receiving RF signals of relatively high signal strength and/or integrity. In this regard, it will be appreciated that in some embodiments the antennas 132 may be spaced apart from one another by at least a quarter of the wavelength of the center frequency at which the RF communication circuit 218 is operating in order to maintain sufficient statistical independence with respect to multipath fading. However, in other embodiments, a quarter wavelength separation is not provided. Various exemplary physical configurations are illustrated in FIGS. 4-10, and will now be described in more detail. Before doing so, however, it will be appreciated that the configurations depicted and described herein are merely exemplary of any one of numerous configurations that can be used to implement the present invention. Moreover, it is once again reiterated that the antennas 132 and RF communication circuit 218 could be implemented in other types of implantable devices that are not configured to deliver medical-type therapy. For example, the implantable device could be a device that functions to relay data transmitted via the RF signals to one or more other implantable devices, which may or may not be IMDs.

Figure 3:
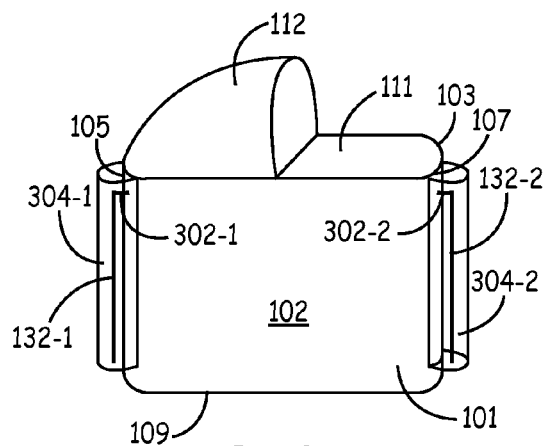
FIGS. 3-10 are various views of various exemplary physical implementations of an IMD illustrating various exemplary configurations and implementations of spatially diverse antennas that may be used with the exemplary circuit of FIG. 2.
Figure 4:
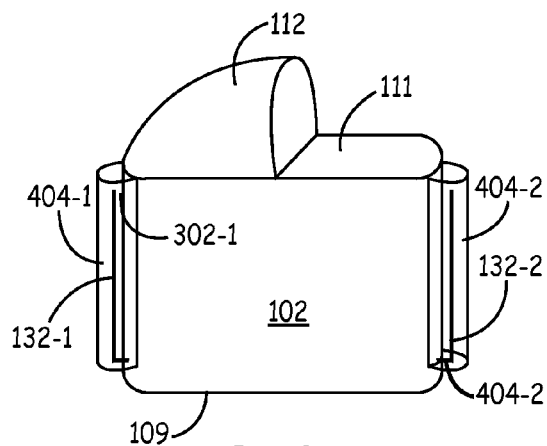

Referring first to FIGS. 3 and 4, the IMDs 100 depicted therein each include two antennas 132-1, 132-2 disposed on opposing sides of the housing 102, and more specifically on the opposing first and second ends 105, 107 of the housing 102. In the embodiment shown in FIG. 3, a pair of antenna feedthroughs 302-1 and 302-2 are disposed on the housing first and second ends 105 and 107, respectively, proximate the housing top surface 111. The feedthroughs 302-1, 302-2 electrically couple one of the antennas 132-1, 132-2 to the communication and control circuit 214 within the housing 102. The embodiment shown in FIG. 4 is similar to that shown in FIG. 3, but the antenna feedthroughs 402-1 and 402-2 are disposed on the housing first and second ends 105 and 107, respectively, proximate the housing bottom surface 109. In both embodiments, the antennas 132-1, 132-2 are preferably each at least partially surrounded by a dielectric material that functions as an antenna radome 304-1, 304-2, 404-1, 404-2. It will be appreciated that the dielectric material may any one of suitable bio-compatible dielectric materials, but in the depicted embodiment the material is tecothane. It will additionally be appreciated that in these embodiments, and the various other embodiments described herein, may be implemented without one or all of the feedthroughs.

Figure 5:
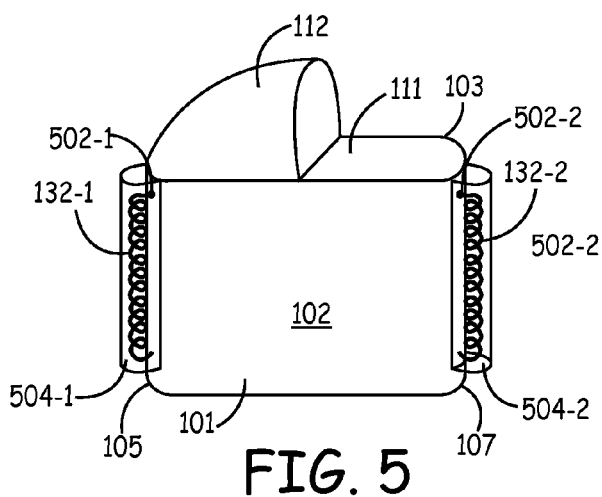

With reference to FIG. 5, yet another exemplary antenna configuration is shown. In this embodiment, the IMD 100 is implemented using two helical antennas 132-1, 132-2 that are disposed on, or proximate, the IMD housing bottom and top surfaces 109 and 111. Similar to the previous embodiments, the antennas 132-1, 132-2 are electrically coupled to the internal communication and control circuit 318 via a pair of antenna feedthroughs 502-1, 502-2, and are at least partially surrounded by a radome 504-1, 504-2. It will be appreciated that the depicted location of the antennas 132-1, 132-2 in FIG. 5 is merely exemplary, and that the antennas 132-1, 132-2 could alternatively be located on the opposing first and second ends 105 and 107, or the opposing first and second side surfaces 101 and 103. No matter the particular physical location, however, the two helical antennas 132-1, 132-2 are preferably configured such that one helical antenna 132-1 is configured orthogonal to the other helical antenna 132-2.

Figure 6:
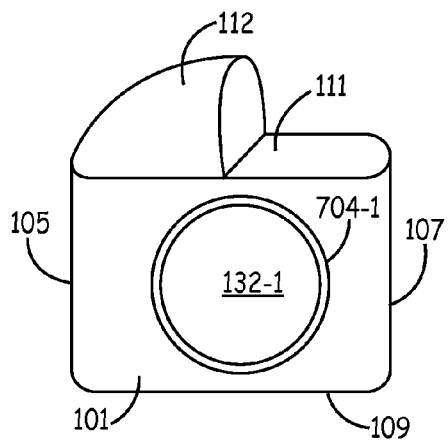
Figure 7:
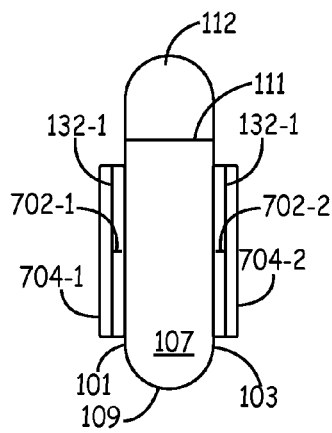

In yet another exemplary physical implementation, which is shown in FIGS. 6 and 7, two patch antennas 132-1, 132-2 are disposed adjacent the opposing first and second housing side surfaces 101, 103. The patch antennas 132-1, 132-2 are centrally disposed adjacent the first and second side surfaces 101, 103, and are each electrically coupled to the communication and control circuit 314 via an associated feedthrough 702-1, 702-2. In the depicted embodiment, the feedthroughs 702-1, 702-2 are centrally disposed on, and extend through, the first and second side surfaces 101, 103. As with the previous embodiments, a radome 704-1, 704-2 at least partially surrounds each patch antenna 132-1, 132-2.

Figure 8:
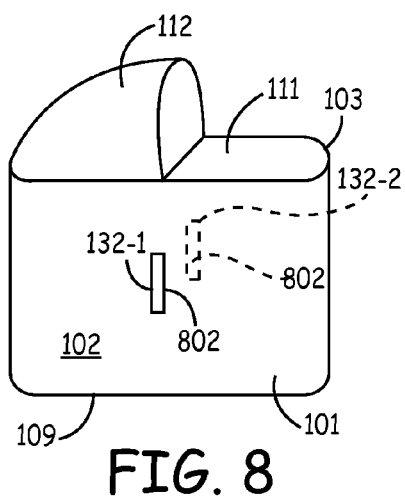

The embodiment depicted in FIG. 8 is similar to that shown in FIGS. 6 and 7, except that the antennas 132-1, 132-2 are implemented as slot antennas. As is generally known, a slot antenna is implemented by forming one or more slot openings 802 in the IMD housing 102 that is configured to emit and receive RF signals to and from, respectively, the IMD 100.

Figure 9:
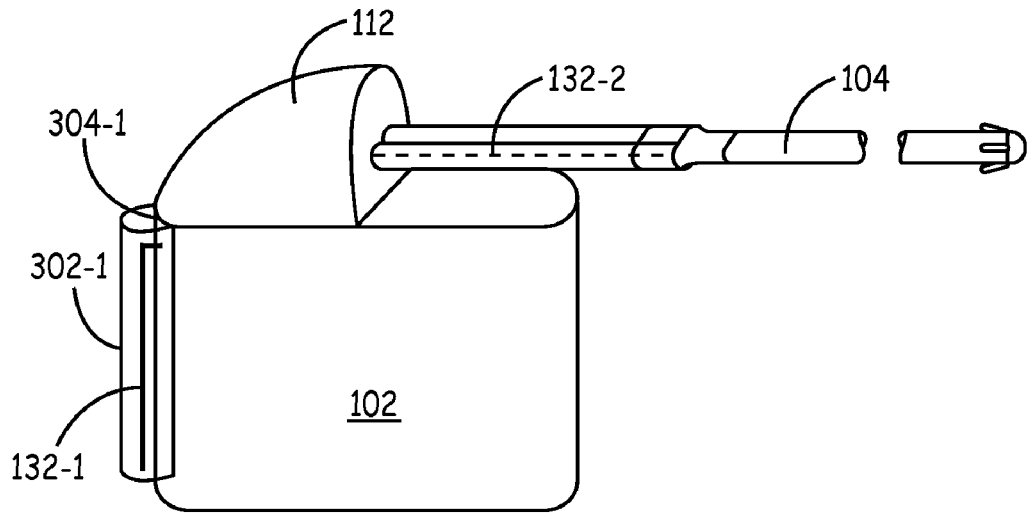
Figure 10:
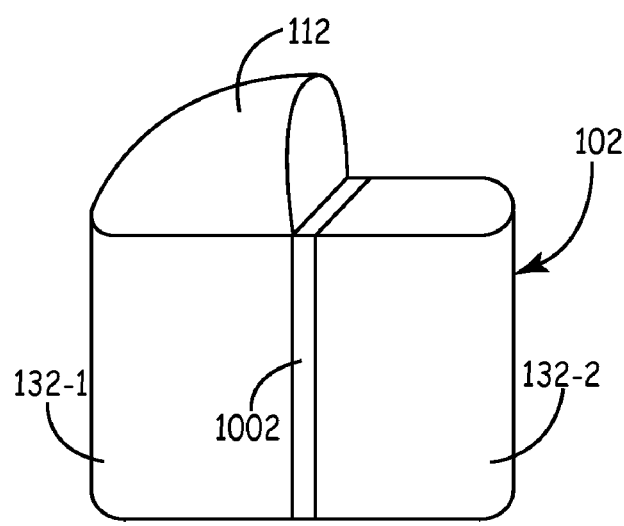

In each of the embodiments depicted in FIGS. 3-8 and described above, each antenna 132-1, 132-2 was disposed on, or at least adjacent to, the IMD housing 102. However, in yet another exemplary embodiment, which is shown in FIG. 9, one of the antennas 132-1 is configured to be part of one of the therapy leads 104-108, while the other antenna 132-2 is configured similar to one of those shown in FIGS. 3 or 4. In yet another exemplary embodiment, which is shown in FIG. 10, two sections of the housing 102 itself are separated from one another by a dielectric 1002, and the housing sections are configured to function as the two antennas 132-1, 132-2.

The antenna configurations described above and shown in FIGS. 3-10 preferably, though not necessarily, provide sufficient spatial diversity to combat the potential effects associated with multipath fading. Yet another advantage these configurations provide is that it allows the IMD 100 to be implanted within a patient in any one of numerous configurations and, with a high degree of probability, remain fully operable to transmit and receive, simultaneously in some instances, RF signals to and from an external transceiver 134. This latter advantage, which may be referred to as pattern diversity, is realized in that the antenna pattern is automatically switched or adjusted to optimize RF signal strength.

While an exemplary embodiment(s) has been presented in the foregoing detailed description of the invention, it should be appreciated that a vast number of variations exist. It should also be appreciated that these exemplary embodiments are only examples, and are not intended to limit the scope, applicability, or configuration of the invention in any way. Rather, the foregoing detailed description will provide those skilled in the art with a convenient road map for implementing a preferred embodiment of the invention. It being understood that various changes may be made in the function and arrangement of elements described in an exemplary preferred embodiment without departing from the spirit and scope of the invention as set forth in the appended claims.

What is claimed is:

1. An implantable medical device (IMD), comprising:
   a housing;
   at least two radio frequency (RF) antennas disposed external and adjacent the housing, each RF antenna configured to receive RF signals transmitted to the IMD from a remote RF signal source, wherein the RF antennas are spaced-apart from one another by a distance that is at least one quarter of the center frequency wavelength;
   an RF communication circuit disposed within the housing and configured to selectively receive the RF signals received by one or more of the RF antennas, wherein the RF communication circuit is configured to operate at a center frequency, the center frequency having a wavelength; and an antenna switch coupled between each of the RF antennas and the RF communication circuit, the antenna switch configured to receive a switch control signal and operable, in response thereto, to selectively couple the RF communication circuit to one of the RF antennas, whereby one of the RF antennas is an active antenna.

2. The device of claim 1, wherein the RF signals received by the active RF antenna have an RF signal strength, and wherein the IMD further comprises:

a communication controller coupled to receive one or more signals at least representative of the received RF signal strength and operable, upon receipt thereof, to selectively supply the switch control signal to the antenna switch.

3. The device of claim 2, wherein:

the one or more signals are one or more data streams having a level of data integrity; and the controller is further operable to (i) determine the level of data integrity of the data streams and (ii) selectively supply the switch control signal, based at least in part on the determined data integrity level.

4. The device of claim 1, wherein each of the RF antennas is disposed external to the housing.

5. The device of claim 1, further comprising:

a plurality of feedthroughs extending through the housing, each feedthrough electrically coupled to one of the RF antennas.

6. The device of claim 1, wherein:

the housing comprises two or more electrically conductive housing sections electrically insulated from one another; and each housing section functions as one of the RF antennas.

7. The IMD of claim 1, wherein:

the RF communication circuit is configured to selectively receive the RF signals received by at least two of the RF antennas; and the RF communication circuit is further operable to combine the RF signals received by the two or more antennas.

8. The device of claim 1, wherein:

the housing includes at least a first side and an opposing second side; and half of the RF antennas are disposed on the first side and half of the RF antennas are disposed on the second side.

9. The device of claim 1, wherein at least two of the RF antennas are disposed, one each, on opposing sides of the housing.

10. The device of claim 1, further comprising:

at least two radomes, each radome at least partially surrounding at least one of the RF antennas.

11. The device of claim 1, further comprising:

a physiological therapy supply circuit disposed within the housing and configured to selectively supply therapy pulses;

one or more therapy leads extending through the housing and coupled to receive the therapy pulses from the physiological therapy supply circuit, wherein at least one of the one or more therapy leads includes one of the RF antennas.

12. The device of claim 1, wherein:

the RF signals are modulated RF signals; and the RF communication circuit is operable, upon receipt of the modulated signals, to demodulate the modulated RF signals.

13. The device of claim 1, wherein the RF antennas are configured to provide spatial diversity.

14. An implantable medical device (IMD), comprising:

a housing;

at least two spatially diverse radio frequency (RF) antennas positioned external and adjacent the housing, each RF antenna configured receive RF signals transmitted to the IMD from a remote RF signal source and to emit RF signals to one or more remote devices;

an RF communication circuit disposed within the housing and configured to selectively receive the RF signals received by one or more of the spatially diverse RF antennas and supply the RF signals emitted by one or more of the spatially diverse antennas; and an antenna switch coupled between each of the RF antennas and the RF communication circuit, the antenna switch configured to receive a switch control signal and operable, in response thereto, to selectively couple the RF communication circuit to one of the RF antennas, whereby one of the RF antennas is an active antenna.

15. The IMD of claim 14, wherein the modulated RF signals received by the active RF antenna have an RF signal strength, and wherein the IMD further comprises:

a communication controller coupled to receive one or more signals at least representative of the received RF signal strength and operable, upon receipt thereof, to selectively supply the switch control signal to the antenna switch.

16. The IMD of 14, wherein:

the antenna switch is operable to selectively couple the RF communication circuit to two or more of the RF antennas; and the RF communication circuit is further operable to combine the RF signals received by the two or more spatially diverse antennas.

17. The IMD of claim 14, wherein:

the housing comprises two or more electrically conductive housing sections electrically insulated from one another; and each housing section functions as one of the spatially diverse RF antennas.

18. The IMD of claim 14, further comprising:

a physiological therapy supply circuit disposed within the housing and configured to selectively supply therapy pulses;

one or more therapy leads extending through the housing and coupled to receive the therapy pulses from the physiological therapy supply circuit, wherein at least one of the one or more therapy leads includes one of the spatially diverse RF antennas.

19. The IMD of claim 14, wherein:

the housing includes at least a first side and an opposing second side; and half of the RF antennas are disposed on the first side and half of the RF antennas are disposed on the second side.

20. The IMD of claim 14, wherein at least two of the RF antennas are disposed, one each, on opposing sides of the housing.

21. The IMD of claim 14, further comprising:

at least two radomes, each radome at least partially surrounding at least one of the RF antennas.

22. The IMD of claim 14, wherein:

the housing includes at least a first side and an opposing second side each having a slot formed therein; and an RF slot antenna disposed within the slot on the first side and the opposing second side to provide spatially diverse radio frequency (RF) antennas.

23. An implantable medical device (IMD), comprising:
a housing having two or more electrically conductive sections electrically insulated from one another;
each housing section functioning as one of at least two spatially diverse radio frequency (RF) antennas, each RF antenna configured receive RF signals transmitted to the IMD from a remote RF signal source and to emit RF signals to one or more remote devices;
an RF communication circuit disposed within the housing and configured to selectively receive the RF signals received by one or more of the spatially diverse RF antennas and supply the RF signals emitted by one or more of the spatially diverse antennas; and
an antenna switch coupled between each of the RF antennas and the RF communication circuit, the antenna switch configured to receive a switch control signal and operable, in response thereto, to selectively couple the RF communication circuit to one of the RF antennas, whereby one of the RF antennas is an active antenna.

24. An implantable medical device (IMD), comprising:
a housing;
a physiological therapy supply circuit disposed within the housing and configured to selectively supply therapy pulses;
at least two spatially diverse radio frequency (RF) antennas, each RF antenna configured receive RF signals transmitted to the IMD from a remote RF signal source and to emit RF signals to one or more remote devices;
one or more therapy leads extending through the housing and coupled to receive the therapy pulses from the physiological therapy supply circuit, wherein at least one of the one or more therapy leads includes a first of the at least two spatially diverse RF antennas;
a second of the at least two spatially diverse RF antennas positioned external and adjacent to the housing;
an RF communication circuit disposed within the housing and configured to selectively receive the RF signals received by one or more of the spatially diverse RF antennas and supply the RF signals emitted by one or more of the spatially diverse antennas; and
an antenna switch coupled between each of the RF antennas and the RF communication circuit, the antenna switch configured to receive a switch control signal and operable, in response thereto, to selectively couple the RF communication circuit to one of the RF antennas, whereby one of the RF antennas is an active antenna.

* * * * *